United States Patent
Xu et al.

(10) Patent No.: US 11,396,642 B2
(45) Date of Patent: Jul. 26, 2022

(54) TUMOUR IMMUNOGEN, PREPARATION METHOD THEREFOR, AND APPLICATION

(71) Applicant: MAGI COMPANY LTD, Shanghai (CN)

(72) Inventors: Xuemin Xu, Shanghai (CN); Ping Liu, Shanghai (CN); Aili Zhang, Shanghai (CN); Jingfeng Bai, Shanghai (CN); Jianqi Sun, Shanghai (CN); Jincheng Zou, Shanghai (CN)

(73) Assignee: MAGI COMPANY LTD, Shanghai (CN)

( * ) Notice: Subject to any disclaimer, the term of this patent is extended or adjusted under 35 U.S.C. 154(b) by 476 days.

(21) Appl. No.: 16/326,428

(22) PCT Filed: Oct. 11, 2017

(86) PCT No.: PCT/CN2017/105727
§ 371 (c)(1),
(2) Date: Apr. 30, 2019

(87) PCT Pub. No.: WO2018/033164
PCT Pub. Date: Feb. 22, 2018

(65) Prior Publication Data
US 2021/0284946 A1    Sep. 16, 2021

(30) Foreign Application Priority Data
Aug. 17, 2016 (CN) .......................... 201610680373.7

(51) Int. Cl.
*C12M 1/34* (2006.01)
*C07K 14/47* (2006.01)
*C12M 1/36* (2006.01)

(52) U.S. Cl.
CPC ............. *C12M 41/12* (2013.01); *C07K 14/47* (2013.01); *C12M 41/48* (2013.01)

(58) Field of Classification Search
CPC ...................................................... C12M 41/48
See application file for complete search history.

(56) References Cited

FOREIGN PATENT DOCUMENTS

| CN | 1709212 A | 12/2005 |
| CN | 102670298 A | 9/2012 |
| CN | 106137378 A | 11/2016 |
| CN | 106220723 A | 12/2016 |

OTHER PUBLICATIONS

Dong et al., Int. J. Hyperthermia, 2009, 25(1):25-33.*
Somersan et al., The J of Immunology, 2001, 167:4844-4852.*
International Search Report and Written Opinion (with English and Chinese) issued in PCT/CN2017/105727, dated Jan. 16, 2018, 21 pages provided.
International Preliminary Report on Patentability (with English and Chinese) issued in PCT/CN2017/105727, dated Feb. 19, 2019, 7 pages provided.
Ren Xiaomin, Study the Biologic Effect of Alternate Thermal Treatments on Tumor, China Master's Theses Full-Text Database, Feb. 2013, School of Biomedical Engineering Shanghai Jiao Tong University, 80 pages, English Abstract provided, cited in the International Search Report.

* cited by examiner

*Primary Examiner* — Bin Shen
(74) *Attorney, Agent, or Firm* — Hamre, Schumann, Mueller & Larson, P.C.

(57) ABSTRACT

Provided are a tumour immunogen, a preparation method therefore, and an application. After localised sequential cooling-heating treatment is performed on tumour tissue and/or cells, the tumour tissue and/or cells release a large amount of tumour immunogen heat shock protein 70. The obtained tumour immunogen can activate the body's tumour immune system, to convert immunosuppressive cells into mature dendritic cells, thereby increasing immunogen presentation, and activating tumour immunity.

9 Claims, 3 Drawing Sheets

TUMOUR IMMUNOGEN, PREPARATION METHOD THEREFOR, AND APPLICATION

TECHNICAL FIELD

The present invention relates to the field of medical engineering, and in particular, the present invention relates to a thermophysical method of stimulating tumor immunogen, especially heat shock protein 70 (HSP70) levels in tumor tissue.

BACKGROUND TECHNIQUE

Malignant tumor cells form a stable structure of tumor immune tolerance so as to protect the tumor cells to escape immune surveillance from the body and to promote the occurrence and development of tumors, by reducing their own immunogenicity, down-regulating expression of co-stimulatory molecules on surface of cells, releasing a large number of immunosuppressive factors, and gathering a variety of immunosuppressive cells. Also, it is the tumor-induced immune tolerance that leads to poor effect of tumor treatment. At the same time, most malignant tumors will cause immunosuppression at different degrees, in order to facilitate tumors to evade body immune surveillance and attack, and promote tumor progression. Numerous studies have shown that immunotherapy for malignant tumor not only eliminates tumors in situ but also has an inhibitory and killing effect on distant metastatic tumor cells. Therefore, a new cancer treatment strategy is getting more and more attention: stimulating the body's anti-tumor function by relieving immunosuppression, so as to obtain better therapeutic effects.

A method which combined cool therapy and thermal therapy was used to enhance local tumor cell necrosis, resulting in cell structure disintegration, and releasing a large number of heat shock protein 70 (HSP70). It is currently believed that heat shock proteins can bind to tumor antigens and induce the body to produce anti-tumor immunity. Heat shock protein 70 (HSP70) is an important protein in heat shock protein family which plays an important role in both innate and acquired anti-tumor immune responses. Studies have shown that the released HSP70 protein can be detected in the body 30 minutes after thermal therapy. Natural killer cells bind to the HSP70 protein on the surface of the tumor cell membrane, which in turn dissolves the tumor cells. The HSP70 protein in tumor cells binds to the tumor antigen to form an immune complex, which is recognized and phagocytosed by the antigen presenting cells (dendritic cells or macrophages) of the body; at the same time, the dendritic cells are activated to promote the maturation of dendritic cells and immune response of the body is obtained.

Therefore, those skilled in the art have been developing a method for improving immunosuppression by promoting a large amount of HSP70 protein in tumor tissues to activate an immune response in a tumor patient.

SUMMARY OF THE INVENTION

The present invention provides a method for stimulating tumors to produce heat shock proteins to activate human immunity and to resist tumors.

In a first aspect of the present invention, a method for promoting the release of tumor immunogen heat shock protein 70 (HSP70) by tumor tissue and/or tumor cells is provided, comprising the steps of:

I) cooling the tumor tissue and/or tumor cells to obtain cooled tumor tissue and/or tumor cells; wherein the cooling comprises cooling the tumor tissue and/or tumor cells to T1, and $-50°$ C.$\leq$T1$\leq$0° C., preferably $-30°$ C.$\leq$T1$\leq$-10° C., more preferably $-25°$ C.$\leq$T1$\leq$-15° C.; most preferably $-20°$ C.$\leq$T1$\leq$-18° C.; and II) heating the cooled tumor tissue and/or tumor cells obtained in I) to obtain heated tumor tissue and/or tumor cells; wherein the heating comprises heating the cooled tumor tissue and/or tumor cells obtained in I) to T2, and 37° C.<T2$\leq$60° C., preferably 40° C.$\leq$T2$\leq$55° C., more preferably 45° C.$\leq$T2$\leq$52° C.

In another preferred embodiment, step I) is a segmented cooling step; and/or
step II) is a segmented heating step.

In another preferred embodiment, in step I), the time required for cooling is S1, and S1$\leq$15 min, preferably S1$\leq$10 min, more preferably S1 is 5-8 min; and/or
in step I), after the temperature reaches T1, it is maintained at T1 for 5-30 min; preferably for 10-25 min; more preferably for 15-20 min.

In another preferred embodiment, in step II), the time required for heating is S2, and S2$\leq$15 min, preferably S2$\leq$10 min, more preferably S2 is 5-8 min; and/or
in step II), after the temperature reaches T2, it is maintained at T2 for 5-30 min; preferably for 10-25 min; more preferably for 15-20 min.

In another preferred embodiment, the cooling and/or heating is linear or non-linear cooling and/or heating.

In another preferred embodiment, step II) further comprises the following sub-steps of segmented heating:

i) heating the cooled tumor tissue and/or tumor cells obtained in I) to T2a, and $-10°$ C.<T2a$\leq$10° C.; preferably $-5°$ C.<T2a$\leq$0° C.; and ii) heating the tumor tissue and/or tumor cells at the temperature of T2a obtained in i) to T2.

In another preferred embodiment, in step i), after the temperature reaches T2a, it is maintained at T2a for 0-5 min; and/or in step ii), after the temperature reaches T2, it is maintained at T2 for 5-30 min; 10-25 min; more preferably, for 15-20 min.

In another preferred embodiment, the method further comprises an optional step of:

III) the cooling step in I) and the heating step in II) are repeated one or more times.

In another preferred embodiment, steps I) and/or II) each further comprise a temperature monitoring step for tumor tissue and/or tumor cells in the method; and/or
steps I) and/or II) each further comprise a quantitative and/or qualitative detection step for a tumor immunogen in the method.

In another preferred embodiment, the temperature monitoring step includes non-invasive monitoring or invasive monitoring. Preferably, the non-invasive monitoring includes infrared image analysis temperature monitoring method, nuclear magnetic resonance temperature detecting method, ultrasonic temperature detecting method.

In another preferred embodiment, the tumor comprises: malignant solid tumor, hematological tumor, benign tumor, metastatic tumor, or combinations thereof.

In another preferred embodiment, the cooling and/or heating comprise cooling and/or heating the tumor cells through direct contact.

In another preferred embodiment, the tumor is preferably a malignant solid tumor.

In another preferred embodiment, the malignant solid tumor comprises gastric cancer, liver cancer, pancreatic cancer, gallbladder cancer, colon cancer, rectal cancer, renal cancer, adrenal gland cancer, malignant skin tumor, chondroma, thyroid cancer, breast cancer.

In another preferred embodiment, the tumor is derived from mammal, such as mouse, rat or human; preferably from human.

In another preferred embodiment, the tumor comprises a tumor isolated from a subject with tumor and/or a tumor located in the body of a subject with tumor.

In another preferred embodiment, the method comprises non-therapeutic method in vitro and/or therapeutic method in vivo.

In a second aspect of the present invention, an apparatus for promoting the release of tumor immunogen by tumor tissue and/or tumor cells is provided, comprising:

a) a cooling element, wherein the cooling element is used for cooling the tumor tissue and/or tumor cells to obtain cooled tumor tissue and/or tumor cells; wherein the cooling comprises cooling the tumor tissue and/or tumor cells to T1, and $-50°\ C.\leq T1\leq 0°\ C.$, preferably $-30°\ C.\leq T1\leq -10°\ C.$, more preferably $-25°\ C.\leq T1\leq -15°\ C.$; most preferably $-20°\ C.\leq T1\leq -18°\ C.$;

b) a heating element, wherein the heating element is used for heating the cooled tumor tissue and/or tumor cells to obtain heated tumor tissue and/or tumor cells; wherein the heating comprises heating the cooled tumor tissue and/or tumor cells obtained in I) to T2, and $37°\ C.<T2\leq 60°\ C.$, preferably $40°\ C.\leq T2\leq 55°\ C.$, more preferably $45°\ C.\leq T2\leq 52°\ C.$;

c) a temperature control element that controls the repetition cycle of the cooling element and the heating element to start and stop, thereby repeating the cooling step and the heating step one or more times;

d) a time control element for controlling the time of cooling, heating and/or temperature maintenance as needed; and optionally e) a temperature monitoring element for monitoring the temperature of tumor tissue and/or tumor cells.

In another preferred embodiment, a temperature feedback element is further disposed between the temperature monitoring element and the temperature control element, and the temperature feedback element is configured to send instructions to start and/or stop the cooling and/or heating steps to the temperature control element after the temperature monitoring element detects that the temperature reaches the set temperature.

In another preferred embodiment, the temperature monitoring element comprises a non-invasive monitor or an invasive monitor, and preferably the non-invasive monitor comprises an infrared image analysis temperature monitor, a nuclear magnetic resonance temperature detector, or an ultrasonic temperature detector.

In another preferred embodiment, the device further comprises tumor immunogen assay element for quantitative and/or qualitative detection of tumor immunogen.

In another preferred embodiment, the cooling element and/or the heating element are each provided with a temperature transmitting element that directly and/or indirectly contacts with tumor tissue and/or tumor cells.

In another preferred embodiment, the indirectly contacting comprises contacting a site close to tumor in the body of a subject with tumor, such as epidermis close to the tumor site.

In a third aspect of the present invention, a method of preparing heat shock protein 70 (HSP70) is provided, comprising the steps of:

A) cooling cultured tumor tissue and/or tumor cells to obtain cooled tumor tissue and/or tumor cells; wherein the cooling comprises cooling the tumor tissue and/or tumor cells to T1, and $-50°\ C.\leq T1\leq 0°\ C.$, preferably $-30°\ C.\leq T1\leq -10°\ C.$, more preferably $-25°\ C.\leq T1\leq -15°\ C.$; most preferably $-20°\ C.\leq T1\leq -18°\ C.$;

B) heating the cooled tumor tissue and/or tumor cells obtained in A) to obtain tumor tissue and/or tumor cell culture containing a cluster of tumor immunogen; wherein the heating comprises heating the cooled tumor tissue and/or tumor cells obtained in A) to T2, and $37°\ C.<T2\leq 60°\ C.$, preferably $40°\ C.\leq T2\leq 55°\ C.$, more preferably $45°\ C.\leq T2\leq 52°\ C.$;

C) heat shock protein 70 (HSP70) isolated and purified from the culture obtained in B).

In a fourth aspect of the present invention, a cluster of tumor immunogen is provided, which comprises tumor immunogens against specific tumor, and the tumor immunogen comprises heat shock protein 70 (HSP70).

In another preferred embodiment, the heat shock protein 70 (HSP70) is prepared by the method of the third aspect of the present invention.

In a fifth aspect of the present invention, use of the heat shock protein 70 (HSP70) of the fourth aspect of the present invention is provided, for preparation of a pharmaceutical composition for preventing and/or treating tumor and/or stimulating organism to produce tumor immunity.

In another preferred embodiment, the pharmaceutical composition is a prophylactic and/or therapeutic vaccine composition.

In another preferred embodiment, the stimulating organism to produce tumor immunity comprises promoting the transformation of immunosuppressive cells into dendritic cells.

In a sixth aspect of the present invention, a pharmaceutical composition is provided, comprising the cluster of tumor immunogen of the fourth aspect of the invention, and a pharmaceutically acceptable carrier.

In another preferred embodiment, the pharmaceutical composition further comprises tumor therapeutic agent such as monoclonal antibody, polyclonal antibody, chemotherapeutic agent and the like.

In a seventh aspect of the present invention, a method for stimulating the production of tumor immunogen, promoting body's tumor immunity, and/or treating a tumor is provided, wherein tumor site of a subject in need is treated according to any method of the first aspects of the present invention, thereby stimulating the production of tumor immunogen, promoting body's tumor immunity, and/or treating a tumor.

In an eighth aspect of the present invention, a method of preventing and/or treating tumor is provided, comprising the steps of: administering the cluster of tumor immunogen of the fourth aspect of the present invention and/or the pharmaceutical composition of the sixth aspect of the present invention to a subject in need, thereby preventing and/or treating tumor.

In a ninth aspect of the present invention, a tumor treatment system is provided, comprising the apparatus according to the second aspect of the present invention, collection device for heat shock protein 70, culture device for mature dendritic cells, and transmission device for mature dendritic cells.

It should be understood that, in the present invention, each of the technical features specifically described above and below (such as those in the Examples) can be combined with each other, thereby constituting new or preferred technical solutions, which needs not be described one by one, due to the space limitation.

DETAILED DESCRIPTION OF THE INVENTION

Figure 1:
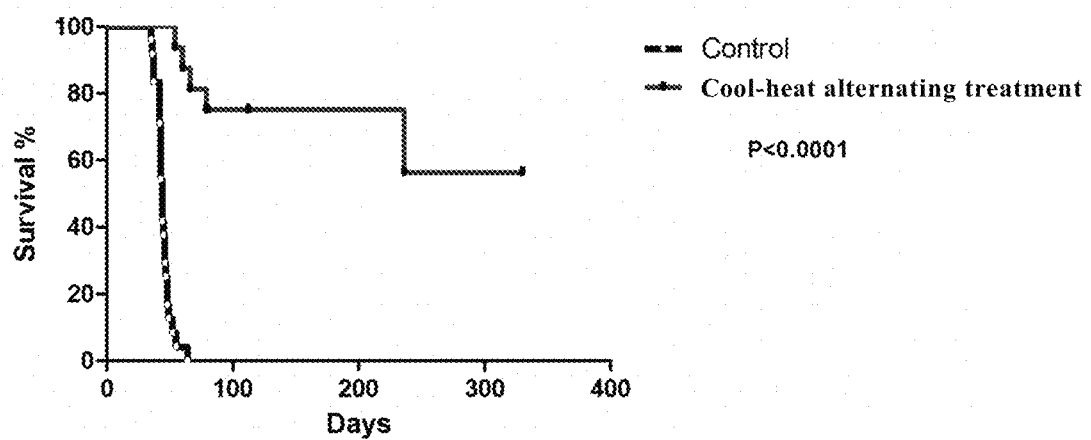
FIG. 1 shows that the survival rate of mice is significantly increased after the cool-heat alternating treatment of the present invention.

Through extensive and intensive research, the present inventors unexpectedly discovered for the first time that tumor tissue and/or cells will release a large amount of tumor immunogen heat shock protein 70 (HSP70) both in vivo and in vitro after undergoing localised sequential cool-heat treatment (or cool-heat treatment), and the amount of the release is significantly larger than the amount produced after only simple thermal stimulation of tumor tissue and/or cells. After the sequential cool-heat treatment of the present invention, the obtained tumor immunogen can effectively activate the tumor immune system in vivo, such as effectively transforming immunosuppressive cells into mature dendritic cells, thereby enhancing the presentation of tumor immunogen and activating tumor immunity. Therefore, the method of the present invention is used for preparing a tumor immunogen, and is administered as a tumor vaccine to a subject in need. Further, the method of the present invention can be directly applied to tumor in vivo, thereby directly obtaining tumor therapeutic effect. The present invention is completed on this basis.

Method for Promoting the Release of Tumor Immunogen by Tumor Tissue and/or Tumor Cells As used herein, the terms "method of the present invention", "cool-heat treatment (treating)" and "sequential cool-heat treatment (treating)" are used interchangeably and refer to the steps according to the first aspect of the invention, i.e., the method of cool-heat treatment of tumor tissues and/or cells in vivo and/or in vitro to obtain a large amount of tumor immunogen, particularly HSP70.

Methods that can be used in the present invention include the following steps:

I) cooling the tumor tissue and/or tumor cells to obtain cooled tumor tissue and/or tumor cells; wherein the cooling comprises cooling the tumor tissue and/or tumor cells to T1, and $-50°$ C.$\leq$T1$\leq$0° C.; and II) heating the cooled tumor tissue and/or tumor cells obtained in I) to obtain heated tumor tissue and/or tumor cells; wherein the heating comprises heating the cooled tumor tissue and/or tumor cells obtained in I) to T2, and 37° C.<T2$\leq$60° C.

In another preferred embodiment, $-30°$ C.$\leq$T1$\leq-10°$ C., more preferably $-25°$ C.$\leq$T1$\leq-15°$ C.; most preferably $-20°$ C.$\leq$T1$\leq-18°$ C.; 40° C.$\leq$T2$\leq$55° C., more preferably 45° C.$\leq$T2$\leq$52° C.

Preferably, the method of the present invention may further comprise the steps of:

III) the cooling step in I) and the heating step in II) are repeated one or more times.

Steps I) and II) which can be used in the method of the present invention can be a segmented cooling and heating step or a one-step cooling and heating step, respectively.

Preferably, step I) is a one-step cooling step. In step I), the time required for cooling is S1$\leq$15 min, preferably S1$\leq$10 min, more preferably S1 is 5-8 min, and after the temperature reaches T1, it is maintained at T1 for 5-30 min; preferably for 10-25 min; more preferably for 15-20 min.

In step II), the time required for heating is S2 and S2$\leq$15 min, preferably S2$\leq$10 min, more preferably S2 is 5-8 min; after the temperature reaches T2, it is maintained at T2 for 5-30 min; preferably, for 10-25 min; more preferably for 15-20 min.

And step II) is preferably a segmented heating step, which may comprise sub-steps:

i) heating the cooled tumor tissue and/or tumor cells obtained in I) to T2a, and $-10°$ C.<T2a$\leq$10° C.; preferably $-5°$ C.<T2a$\leq$0° C.; and ii) heating the tumor tissue and/or tumor cells at the temperature of T2a obtained in ii) to T2.

After the temperature reaches T2a in step i), it is maintained at T2a for 0-5 min; and/or after reaching T2 in step ii), it is maintained at T2 for 5-30 min; 10-25 min; more preferably, for 15-20 min. In step ii), after the temperature reaches T2, it is maintained at T2 for 5-30 min; 10-25 min; more preferably, for 15-20 min.

When the step II) is a one-step heating step, the time required for heating in step II) is S2 and S2$\leq$15 min, preferably S2$\leq$10 min, more preferably S2 is 5-8 min, and after reaching T2, it is maintained at T2 for 5-30 min; 10-25 min; more preferably for 15-20 min.

In the present invention, direct or indirect temperature adjustment, preferably direct temperature adjustment, may be applied to the tumor tissue and/or tumor cells, such as cooling or heating the tumor tissue by being contacted with a cooling or heating element. When the method of the invention is used in vivo, the cooling or heating element can be contacted with tumor tissue (e.g., intraoperatively) or placed near the local epidermis adjacent to tumor tissue.

Furthermore, in the method of the present invention, the generated tumor immunogen and/or the temperature of the tumor tissue and/or cells can also be monitored in each step, thereby adjusting the temperature and the maintenance time in each step in time. The temperature monitoring step includes non-invasive monitoring or invasive monitoring. Preferably, the non-invasive monitoring includes infrared image analysis temperature monitoring, nuclear magnetic resonance temperature detecting, or ultrasonic temperature detecting. Other temperature monitoring methods which are well known to those skilled in the art can also be used in the temperature monitoring of the present invention. Monitoring of tumor immunogen can be performed quantitatively and/or qualitatively using non-invasive and/or invasive methods, such as quantitative or qualitative monitoring of tumor immunogen in tumor interstitial fluid or in organismal samples (eg, serum), by immunohistochemistry, ELISA, for example, which are well known to those skilled in the art.

The type of tumor which can use the method of the present invention is not particularly limited. Any tumor that can produce tumor immunogens can be used in the method of the present invention. Preferred tumor types include malignant solid tumors, hematological tumors, metastatic tumor, or a combination thereof. In addition, benign tumors can also apply the method of the invention.

Tumor Immunogen Heat Shock Protein 70 (HSP70)

Heat shock protein 70 (HSP70) is an important family protein in heat shock proteins which plays an important role in both innate and acquired anti-tumor immune responses. Studies have shown that the released HSP70 protein can be detected in the body 30 minutes after thermal therapy. Natural killer cells bind to the HSP70 protein on the surface of the tumor cell membrane, which in turn dissolves the tumor cells. The HSP70 protein in tumor cells binds to the tumor antigen to form an immune complex, which is recognized and phagocytosed by the antigen presenting cells (dendritic cells or macrophages) of the body; at the same time, the dendritic cells are activated to promote the maturation of dendritic cells and immune response of the body is obtain. Pharmaceutical composition for treating or preventing a tumor, such as vaccine composition, can be prepared using the tumor immunogen heat shock protein 70 of the present invention. The antigen presenting cells of the body are activated after administration (for example, intravenous infusion) to a subject in need, thus activating the body's tumor immune activity.

Apparatus of the Present Invention

The invention also provides an apparatus for carrying out the method of the present invention, wherein the apparatus comprises a) a cooling element, wherein the cooling element is used for cooling the tumor tissue and/or tumor cells to obtain cooled tumor tissue and/or tumor cells; wherein the cooling comprises cooling the tumor tissue and/or tumor cells to T1, and $-50°$ C.$\leq$T1$\leq$0° C., preferably, $-30°$ C.$\leq$T1$\leq$$-10°$ C., more preferably $-25°$ C.$\leq$T1$\leq$$-15°$ C.; most preferably, $-20°$ C.$\leq$T1$\leq$$-18°$ C.;

b) a heating element, wherein the heating element is used for heating the cooled tumor tissue and/or tumor cells to obtain heated tumor tissue and/or tumor cells; wherein the heating comprises heating the cooled tumor tissue and/or tumor cells obtained in I) to T2, and 37° C.$\leq$T2$\leq$60° C., preferably 40° C.$\leq$T2$\leq$55° C., more preferably 45° C.$\leq$T2$\leq$52° C.;

c) a temperature control element that controls the repetition cycle of the cooling element and the heating element to start and stop, thereby repeating the cooling step and the heating step one or more times; and optionally d) a temperature monitoring element for temperature monitoring of tumor tissue and/or tumor cells.

The cooling element and/or the heating element and/or the temperature control element and/or the temperature monitoring element which can be used in the present invention are not particularly limited, and may be any element in the art which can be used for medical treatment or temperature adjustment of cells.

Preferably, a temperature feedback element is further disposed between the temperature monitoring element and the temperature control element, and the temperature feedback element is configured to send instructions to start and/or stop the cooling and/or heating steps to the temperature control element after the temperature monitoring element detects that the temperature reaches the set temperature. The temperature monitoring element comprises a non-invasive monitor or an invasive monitor. Preferably the non-invasive monitor comprises an infrared image analysis temperature monitor, a nuclear magnetic resonance temperature detector, or an ultrasonic temperature detector. In addition, the apparatus further comprises tumor immunogen assay element for quantitative and/or qualitative detection of tumor immunogen.

Preferably, the cooling element and/or the heating element are each provided with a temperature transmitting element that directly and/or indirectly contacts with tumor tissue and/or tumor cells.

Preparation Method of Tumor Immunogen

The invention also provides a method for preparing tumor immunogen (especially HSP70), wherein the tumor immunogen is separated and purified from the tumor cell culture medium after cool-heat treatment of the tumor cells cultured in vitro, based on the sequential cool-heat treatment of the present invention. Preferably, the preparation method of the present invention comprises:

A) cooling cultured tumor tissue and/or tumor cells to obtain cooled tumor tissue and/or tumor cells; wherein the cooling comprises cooling the tumor tissue and/or tumor cells to T1, and $-50°$ C.$\leq$T1$\leq$0° C., preferably $-30°$ C.$\leq$T1$\leq$$-10°$ C., more preferably $-25°$ C.$\leq$T1$\leq$$-15°$ C.; most preferably, $-20°$ C.$\leq$T1$\leq$$-18°$ C.;

B) heating the cooled tumor tissue and/or tumor cells obtained in A) to obtain tumor tissue and/or tumor cell culture containing a cluster of tumor immunogen; wherein the heating comprises heating the cooled tumor tissue and/or tumor cells obtained in A) to T2, and 37° C.<T2$\leq$60° C., preferably 40° C.$\leq$T2$\leq$55° C., more preferably 45° C.$\leq$T2$\leq$52° C.;

C) isolating and purifying the tumor immunogen from the culture obtained in B).

It is preferred to isolate and purify tumor immunogen after obtaining a cell culture solution containing the tumor immunogen of the present invention. The method used may be conventional techniques in the art, and one or more tumor immunogens can be isolated or purified.

Pharmaceutical Composition

The present invention also provides a pharmaceutical composition comprising a safe and effective amount of tumor immunological antigen cluster and a pharmaceutically acceptable carrier or excipient. Such carriers include, but are not limited to, saline, buffer solution, glucose, water, glycerin, ethanol or a combination thereof. The pharmaceutical preparation should be matched to the method of administration. The pharmaceutical composition of the present invention can be prepared in the form of injection, for example, prepared by a conventional method using physiological saline or an aqueous solution containing glucose and other adjuvants. Pharmaceutical compositions such as injections, solutions, lyophilized preparations are preferably prepared under sterile conditions. The dosage of active ingredient is therapeutically effective amount, for example from about 1 microgram per kilogram body weight to about 5 milligrams per kilogram body weight per day. In addition, the cluster of tumor immunological antigen of the present invention may also be used together with other therapeutic agents (e.g., tumor inhibitor such as monoclonal antibodies, polyclonal antibodies, chemotherapeutic agents, etc.).

When the pharmaceutical composition is used, a safe and effective amount of the tumor immunogen cluster of the invention is administered to a mammal, wherein the safe and effective amount is usually at least about 10 micrograms per kilogram of body weight, and in most cases does not exceed about 8 mg/kg body weight, and preferably the dose is about 10 micrograms/kg body weight to about 1 mg/kg body weight. Of course, the particular dose should also depend on various factors, such as the route of administration, patient's health status, which are well within the skills of an experienced physician.

Beneficial Effects of the Present Invention (1) The present invention discloses a method for promoting large secretion of tumor immunogen HSP70 by tumor cells for the first time, which can be effectively applied to the preparation of tumor vaccine, and can also be directly used in immunotherapy on a tumor-affected individual.

(2) The antigen obtained by the method of the present invention can effectively promote maturation of immunosuppressive cells and activate anti-tumor immune response. The experiment result shows that the maturation and differentiation of immunosuppressive cells to dendritic cells in mice can be promoted using the method of the present invention to treat tumor-bearing mice.

(2) The survival rate of tumor-bearing mice can be significantly increased using the method of the present invention to treat tumor-bearing mice.

The present invention will be further illustrated below with reference to the specific examples. It should be understood that these examples are only to illustrate the invention but not to limit the scope of the invention. For the experimental methods in the following examples the specific conditions of which are not specifically indicated, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified. Unless indicated otherwise, parts and percentage are weight parts and weight percentage.

General Materials and Methods

1. Animals, Cell Lines and Main Reagents

SPF Balb/c female mice aged 6-8 weeks (Shanghai Slac Animal Center) were kept in a separate ventilation box cage. An artificially control light of 12 hrs day light and 12 hrs night light was used. The mice could freely take feed sterilized with 60Co radiation and water sterilized with high temperature. Mouse 4T1 breast cancer cells (obtained from Shanghai First People's Hospital and other breast cancer cells such as T47D cell line in other embodiments) were cultured in DMEM medium (Hyclone Co., USA) supplemented with 10% newborn fetal bovine serum and double antibiotics (100 U/mL penicillin and 100 g/mL streptomycin) (Shanghai Biotechnology Engineering Co., Ltd.). Magnetic beads for immune cell sorting were purchased from Miltnyi Biotec Co., Germany. AF488 anti-mouse CD11c, APC anti-mouse F4/80, Percp/cy5.5 anti-mouse CD86, PE anti-mouse MHC II for flow cytometry were purchased from Biolegend.

2. Establishment of 4T1 Breast Cancer Model and Measurement of Tumor Size

The 4T1 mouse breast cancer cell used in this study is capable of metastasis to lungs, liver, bone marrow and brain via hematogenous pathways, and is a model of highly metastatic breast cancer. $1 \times 10^6$ U/0.1 mL of 4T1 cells suspension was prepared and placed on ice. Mice were anesthetized by intraperitoneal injection of 0.016 g/mL pentobarbital sodium in a dose of 0.5 mL/100 g mice, and 0.1 mL cell suspension was subcutaneously injected into the back of mice. 21 days after tumor inoculation, the tumor volume was measured with a vernier caliper, and calculated according to the following formula: V $(cm^3) = \pi/6 \times$ long axis of tumor (cm)×short axis of tumor (cm)×tumor height (cm).

3. Evaluation on Efficacy of Cool-Heat Treatment

After treatment, the survival status of mice was observed comprehensively. This part of study mainly included: observation of in situ tumor growth in control group, in situ tumor ablation and recurrence in treatment group and metastasis of mice in each group (daily), records of change of body weight of mice before and after treatment (twice a week), statistics of long-term survival percentage and survival time of mice. These indicators could effectively reflect survival of mice, wherein statistics of survival percentage and survival time were the most important indicators for evaluation of treatment.

4. Western Blot Analysis of Tumor Interstitial Fluid

The mouse tumors were taken 1 day after cool-heat treatment, and the tumors of control mice were taken 22 days after inoculation. The tumors were wrapped with filter membrane and placed in 15 ml centrifuge tube, and centrifuged at 2000 rpm for 15 minutes. The interstitial fluid at the bottom of centrifuge tube was aspirated. The total amount of protein was determined by Bradford method. 30 μs of protein was extracted and added to a 4-20% gradient glycine precast gel electrophoresis, and transferred to a PVDF membrane. HSP70 primary antibody (Cell signaling technology) and fluorescent secondary antibody were incubated. The exposed blotting bands were recorded.

5. Tumor Immunohistochemical Staining

The mice tumors were taken 1 day after cool-heat treatment or single heat treatment, and the tumors of control mice were taken 22 days after inoculation. The tumor was quickly frozen with isopentane, and then put into tin foil and store in a refrigerator at −80° C. The tumor was removed and fixed on the sample holder with OCT embedding glue. The tumor was cut into 10 μm slices at an ambient temperature of −20° C. using a freezing microtome. The slices were adhered to a cover glass and stored in a −80° C. refrigerator. The tumor slices were naturally air-dried, and then fixed in acetone for 10 minutes at 4° C. and rinsed with PBS. The slices were inactivated with 0.3% peroxidase ($H_2O_2$ solution diluted with methanol) for 20 minutes and rinsed with PBS. 5% BSA was dropwise added and the slices were blocked for 30 minutes. Primary antibody anti-HSP70 (Abcam, diluted 1:1000 with PBS) was added. Then the slices were incubated for 1 hour at 37° C. and rinsed with PBS. Biotin-labeled secondary antibody was added. Then the slices were incubated at 37° C. for 1 hour. Streptavidin-HRP and peroxidase substrate diaminobenzidine (DAB) in an immunohistochemistry detection kit were used for staining. Hematoxylin was used for counterstained. The slices were observed, photographed and recorded under the bright field of the microscope.

6. Detection of HSP70 in Peripheral Serum by ELISA

Two days after the treatment, blood was collected from eyeball veins of mice in cool-heat treatment group, tumor surgical resected group, single heat treatment group and control group without any treatment. The collected venous blood was allowed to stand for 1 hour, centrifuged at 2000 rpm for 20 minutes, and the supernatant serum was extracted. Serum samples were processed according to the request of ELISA test samples to detect the expression of HSP70 in serum.

7. Magnetic Bead Sorting of Immunosuppressive Cells 2 days and 10 days after cool-heat treatment, the mouse spleen was taken, and the spleen cell suspension was obtained using GentleMACS gentle tissue processor. The suspension was centrifuged at 1500 rpm for 5 minutes and the supernatant was discarded. 2 ml of red blood cell lysate was added. Then the mixture was blowed and mixed equably, and lysed for 5 minutes at room temperature. PEB was added to dilute the mixture as much as possible and then centrifuge the mixture to remove the supernatant to obtain spleen cells. Immunosuppressive cells with purity greater than 90% were sorted using the immunosuppressive cell Kit of Miltnyi Biotec, Germany for experiments.

8. Differentiation Experiment of Immunosuppressive Cell 8.1 In Vivo Experiments 10 days after cool-heat treatment, the spleens of mice were taken, and the spleens of mice in control group were also taken. Immunosuppressive cells were sorted from spleen cells by magnetic bead sorting. CD11c and F4/80 were used as surface marker antigens of dendritic cells and macrophages, respectively, and CD86 and MHC II were used as surface marker antigens of maturation of both cells. 1 μl of corresponding fluorescent antibody was added and cells were incubated at 4° C. for 30 minutes in the dark. After being washed with PBS, cells were resuspended and detected by flow cytometry.

8.2 Serum Collection of In Vitro Experiments

Blood was collected from eyeball veins of the mice in treatment group 2 days after cool-heat treatment, the mice in control group and the mice in normal group. The collected venous blood was allowed to stand for 1 hour, centrifuged at 2000 rpm for 20 minutes, and the supernatant serum was aspirated and stored at minus 80 degrees Celsius.

8.3 In Vitro Experiments 23 days after inoculation, the immunosuppressive cells were sorted from the spleens of mice in control group by magnetic beads, and were incubated for four hours with DMEM mediums added with the mouse serum of treatment group, the mouse serum of control group, the mouse serum of normal mice, and the serum of treatment group+HSP70 antibody, respectively. Flow cytometry was used to detect the expression of cell surface marker antigens CD11c, F4/80, CD86 and MHC II.

9 Data Statistics

The statistics and analysis of all experimental datas in experiments were performed by using Graph pad Prism software, and Student's t test was used to analyze the difference between groups. The results were shown as mean±standard deviation. If $P<0.05$, it was considered as significant difference between the data.

Example 1 Cool-Heat Treatment Improves Mouse Survival Rate

The mice in the cool-heat treatment group (n=16) were treated with cool-heat treatment, in which the temperature was lowered to −20° C. in 10 minutes, and maintained for 5 minutes, and then heated to 50° C. in 10 minutes and maintained for 20 minutes.

The blank control mice (n=16) were not treated.

The survival status of the mice in the cool-heat treatment group and the blank control was observed for one year (FIG. 1). The survival time of the 16 cool-heat treated mice was longer than 66 days after the inoculation, and 11 mice survived to one year in final. The survival time of the 16 control mice did not exceed 64 days after inoculation.

Figure 2:
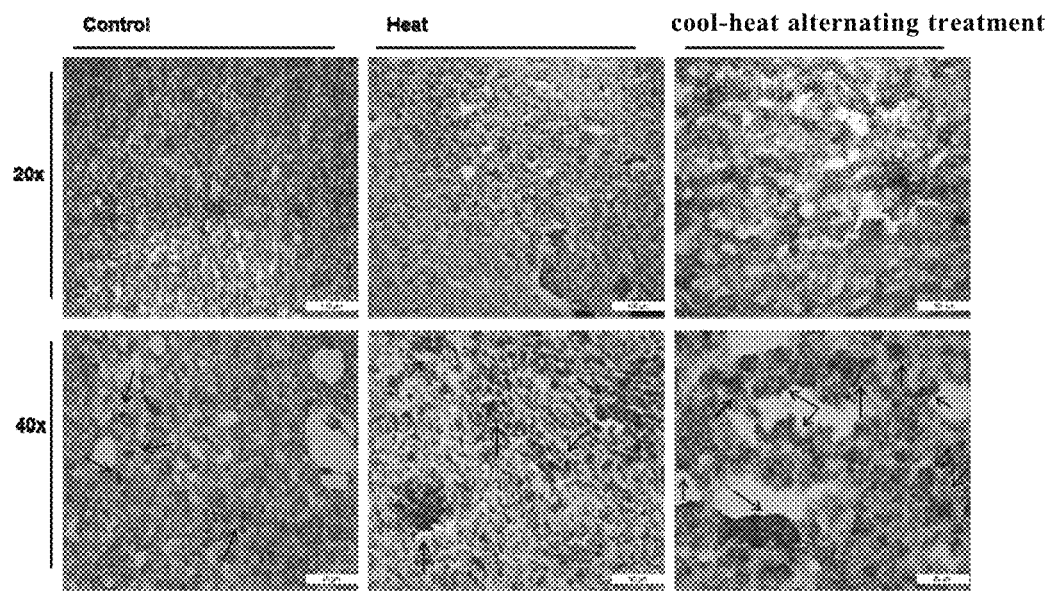
FIG. 2 shows that a large amount of HSP70 is released from tumor tissue after the cool-heat alternating treatment of the present invention.

Example 2 Cool-Heat Treatment Promotes the Release HSP70 in Local Tumor 1 day after cool-heat treatment and single heat treatment in Example 3 and 22 days after inoculation, in situ tumor sections were taken for immunohistochemistry. (FIG. 2) Brown (light) is the specific staining of the HSP70 protein by the antibody, and blue (dark) is the staining of the nuclei by hematoxylin.

In the control group, the presence of some isolated HSP70 was observed and was mostly present in the cells and was not released. Such HSP70 mainly played a role in promoting tumor cell survival.

The release of regional HSP70 was observed in both the signal heat treatment group and the cool-heat treatment group. But the release area of HSP70 was limited in the single heat treating group, and some areas with intact nucleus, HSP70 was not released.

Cell necrotic death and cell disruption were severe in the cool-heat treatment group, which was accompanied by a larger release area of HSP70. In conclusion, the experimental results demonstrated that cool-heat treatment acts on tumors in situ, which induces more release of HSP70 at the same time as more severe cell necrotic death.

Figure 3:
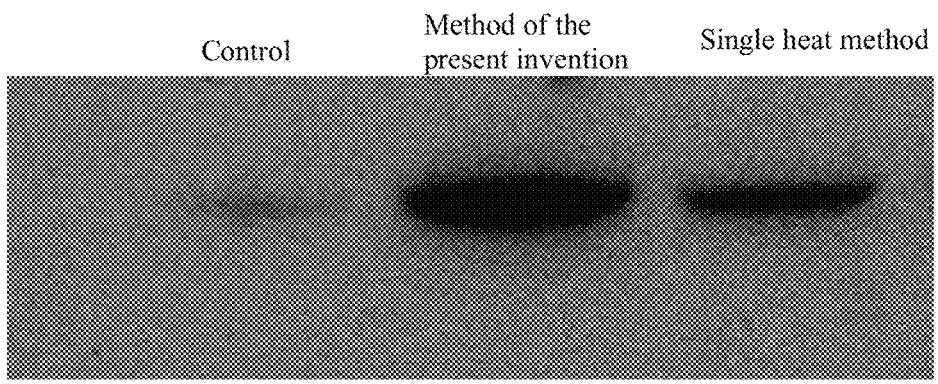
FIG. 3 displays the result of western blot analysis of tumor interstitial fluid, which shows that a large amount of HSP70 protein was released in the cool-heat treatment group.

Western blot analysis of tumor interstitial fluid showed that the HSP70 protein level in the cool-heat treatment group was significantly higher than that in the control group. (FIG. 3)

Figure 4:
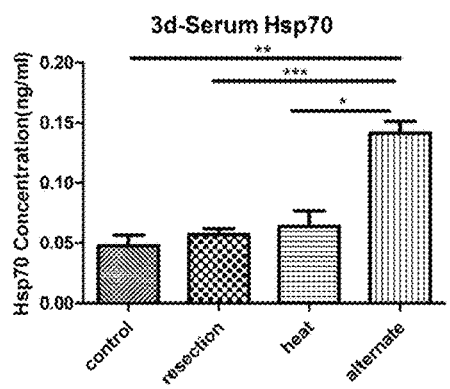
FIG. 4 shows that the HSP 70 level in peripheral blood of mice in the cool-heat treatment group is significantly increased.

The ELISA test showed that the HSP70 level in the serum of the surgical group was slightly lower than that of the control group, 2 days after the treatment of orthotopic tumor resection. The HSP70 level in the serum of single heat treatment group showed small difference than that of the control group. The increase of HSP70 level was more obvious in peripheral blood serum of the cool-heat treatment group. (FIG. 4)

Figure 5:
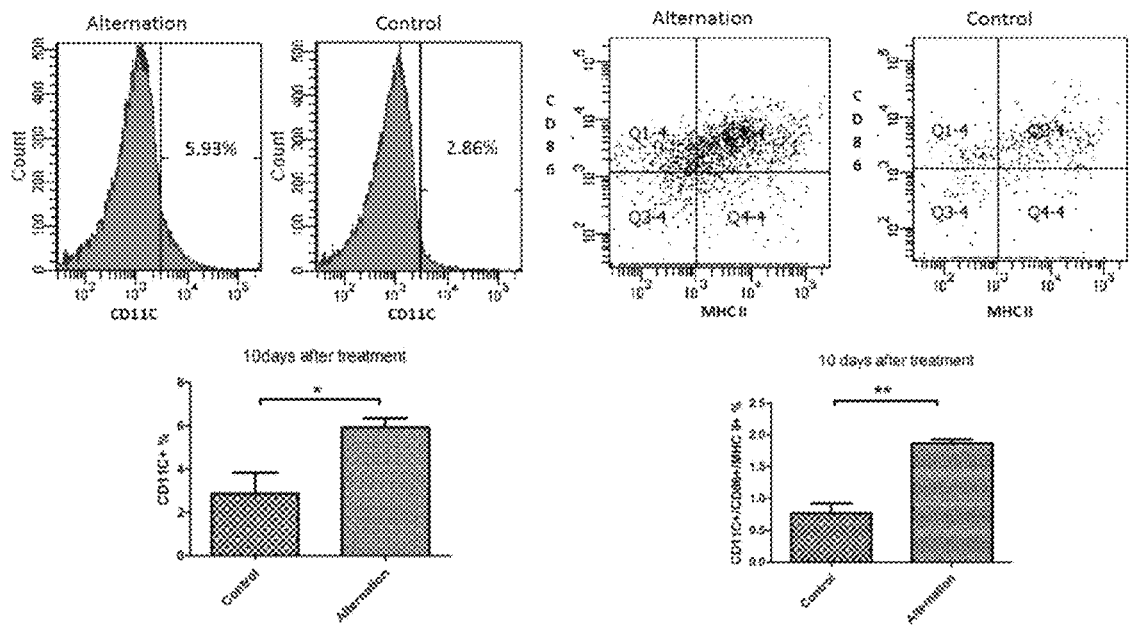
FIG. 5 shows that cool-heat treatment promotes the transformation of immunosuppressive cells MDSC into mature dendritic cells.

Example 3 Cool-Heat Treatment Promotes Maturation and Differentiation of Immunosuppressive Cells 3.1 In Vivo Experiments 10 days after the cool-heat treatment, the expression level of CD11C on the surface of spleen immunosuppressive cells in the cool-heat treatment group was higher than that in the control group. The expression levels of MHC II and CD86 on the surface of immunosuppressive cells in the cool-heat treatment group were significantly higher than those in the control group. (FIG. 5) It indicates that cool-heat treatment promotes the transformation of immunosuppressive cells MDSC into mature dendritic cells.

3.2 In Vitro Experiments

Figure 6:
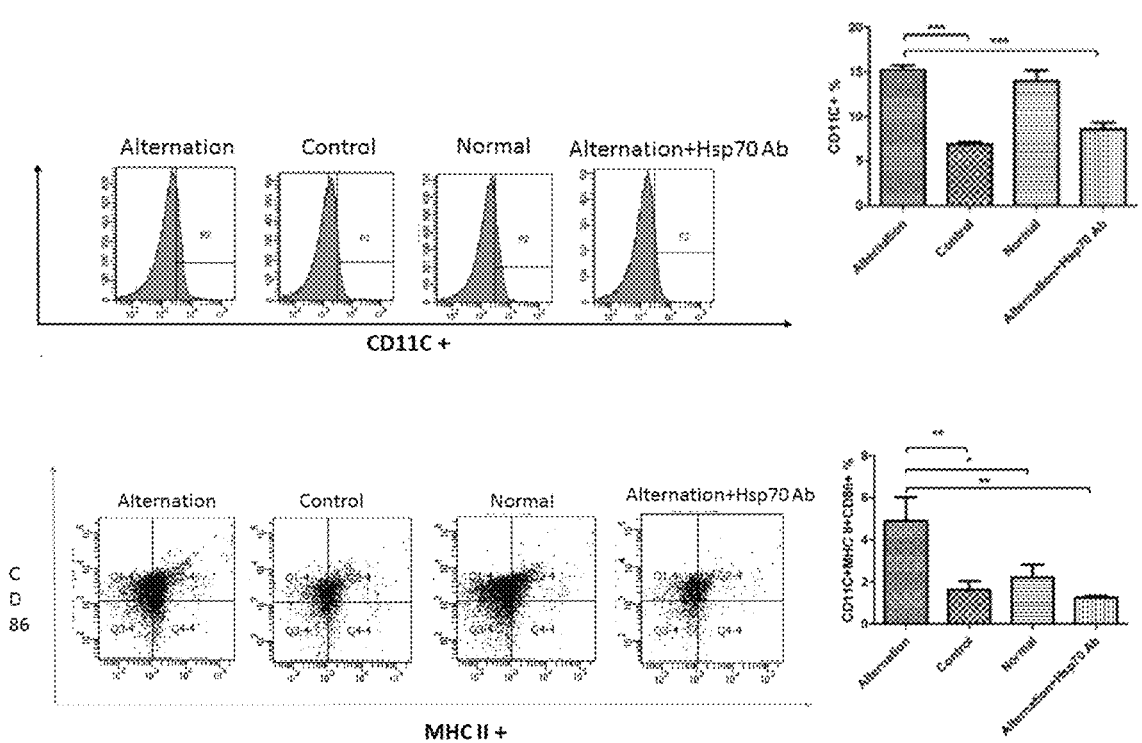
FIG. 6 shows that after cool-heat treatment, HSP70 in serum promotes the transformation of immunosuppressive cells MDSC into mature dendritic cells.

After the immunosuppressive cells were incubated with four serum media for 24 hours, the expression level of CD11C on the surface of the immunosuppressed cells incubated with the serum of the cool-heat treatment group was significantly higher than that of the control group and the cool-heat treatment group with HSP70 neutralizing antibody added, which showed no difference with that of the immunosuppressive cells incubated with normal mice serum. (FIG. 6) Flow cytometry results showed that the expression levels of CD86 and MHC II on the surface of the immunosuppressive cells incubated with the serum of the cool-heat treatment group was significantly higher than that of the control group and the cool-heat treatment group with HSP70 neutralizing antibody added; and higher than that of the immunosuppressive cells incubated with normal mice serum. It indicates that HSP70 in serum promotes the transformation of immunosuppressive cells MDSC into mature dendritic cells after cool-heat treatment.

All literatures mentioned in the present application are incorporated herein by reference, as though each one is individually incorporated by reference. In addition, it should also be understood that, after reading the above teachings of the present invention, those skilled in the art can make various changes or modifications, equivalents of which falls in the scope of claims as defined in the appended claims.

The invention claimed is:

1. A method for transforming myeloid-derived suppressor cells (MDSCs) into mature dendritic cells, comprising:
   (A) cooling a cultured tumor tissue and/or tumor cells to obtain a cooled tumor tissue and/or tumor cells, wherein the cooling comprises cooling the tumor tissue and/or the tumor cells to T1, where $-30° C.\leq T1 \leq -10° C.$;
   (B) heating the cooled tumor tissue and/or tumor cells obtained in (A) to obtain a tumor tissue and/or tumor cell culture containing a cluster of tumor immunogen, wherein the heating comprises heating the cooled tumor tissue and/or tumor cells obtained in (A) to T2, where $40° C. < T2 \leq 55° C.$;
   (C) isolating and purifying a heat shock protein 70 (HSP70) from the tumor tissue and/or tumor cell culture obtained in (B); and
   (D) contacting the HSP70 obtained in (C) with MDSCs to effectively transform MDSCs into mature dendritic cells.

2. The method of claim 1, wherein
   (A) is a segmented cooling step; and/or
   (B) is a segmented heating step.

3. The method of claim 1, wherein a time required for reaching T1 in (A) is S1, where $S1 \leq 15$ min; and
   in (A), after a temperature of the tumor tissue and/or tumor cells reaches T1, the temperature is maintained at T1 for 5-30 min.

4. The method of claim 1, wherein a time required for reaching T2 in (B) is S2, and $S2 \leq 15$ min; and
   in (B), after a temperature of the cooled tumor tissue and/or tumor cells reaches T2, the temperature is maintained at T2 for 5-30 min.

5. The method of claim 1, wherein the heating in (B) comprises:
   i) heating the cooled tumor tissue and/or tumor cells obtained in (A) to T2a, where $-10° C. < T2a \leq 10° C.$; and
   ii) heating the tumor tissue and/or tumor cells at the temperature of T2a obtained in i) to T2.

6. The method of claim 1, wherein
   the cooling in (A) and the heating in (B) are optionally repeated one or more times.

7. The method according to claim 1, wherein (A) and/or (B) each further comprises:
   monitoring a temperature of the tumor tissue and/or tumor cells, the monitoring includes a non-invasive monitoring or an invasive monitoring, the non-invasive monitoring includes an infrared image analysis temperature monitoring method, a nuclear magnetic resonance temperature detecting method, and an ultrasonic temperature detecting method; and
   quantitative and/or qualitative detection for a tumor immunogen.

8. The method of claim 1, wherein the tumor comprises malignant solid tumor, hematological tumor, benign tumor, metastatic tumor, or combinations thereof.

9. The method of claim 1, wherein the phenotype of the mature dendritic cells is CD11C+CD86+MHCII+.

* * * * *